United States Patent [19]

Scarbrough et al.

[11] Patent Number: 4,998,912

[45] Date of Patent: Mar. 12, 1991

[54] DIVERGING GYNECOLOGICAL TEMPLATE

[75] Inventors: Edward C. Scarbrough, Irving; Pietro P. Antich, Richardson; Berchmans John, Grand Prairie; Phuc D. Nguyen, Dallas, all of Tex.

[73] Assignee: Board of Regents, The University of Texas System, Austin, Tex.

[21] Appl. No.: 317,775

[22] Filed: Mar. 2, 1989

[51] Int. Cl.⁵ .............................................. A01N 5/00
[52] U.S. Cl. .......................................... 600/6; 600/4
[58] Field of Search ............................. 600/1, 3, 6–8; 606/130, 150

[56] References Cited

U.S. PATENT DOCUMENTS

| | | | |
|---|---|---|---|
| 3,135,263 | 6/1964 | Connelley, Jr. | 128/303 |
| 3,508,552 | 4/1970 | Hainault | 128/303 |
| 3,741,205 | 6/1973 | Markolf | 128/92 B |
| 3,750,653 | 8/1973 | Simon | 128/1.2 |
| 3,817,249 | 6/1974 | Nicholson | 128/303 |
| 4,167,179 | 9/1979 | Kirsch | 128/1.2 |
| 4,427,005 | 1/1984 | Tener | 128/303 |
| 4,434,789 | 3/1984 | Kumar | 128/1.2 |
| 4,586,490 | 5/1986 | Katz | 128/1.1 |

OTHER PUBLICATIONS

A. Martinez et al., "A Multiple-Site Perineal Applicator (MUPIT) for Treatment of Prostatic, Anorectal and Gynecologic Malignancies," *Int. J. Radiation Oncology Biol. Phys.*, 10:297–305 (1985).

A. M. N. Syed et al., "Transperineal Interstitial-Intracavitary 'Syed–Neblett' Applicator in the Treatment of Carcinoma of the Uterine Cervix," *Endocurie, Hypertherm, Oncol.*, 2:1–13 (1987).

J. Berchmans et al., "A Diverging Gynecological Template for Radioactive Interstitial/Intracavitary Implants of the Cervix", *Int. J. Radiation Oncology Biol. Phys.*, 15:461–465 (1988).

*Primary Examiner*—Randall L. Green
*Assistant Examiner*—Kim Reichle
*Attorney, Agent, or Firm*—Baker & Botts

[57] ABSTRACT

A diverging template (18) for radioactive therapy of cancer within an internal tumor volume by interstitial implants through the skin (78) comprises a proximal surface (34) for positioning adjacent the skin and a distal surface (36) opposite the proximal surface (34). An axis (32) of the template (18) is substantially perpendicular to the proximal surface (34). A plurality of holes (24'-30') are formed in the template (18) from the distal surface (36) to the proximal surface (34) for guiding respective needles (24-30) through the skin (78) and into the tumor volume. The holes comprise at least a first group (28) and a second group (26), each hole of the first group (28) spaced from the axis (32) and forming a first angle therewith that diverges from the distal surface (36) to the proximal surafce (34). Each hole (26) of the second group is spaced from the axis (32) and diverges from the distal surface (36) to the proximal surface (34) at a second angle greater than the first angle. The template of the invention allows the treatment of an internal tumor volume that is greater in lateral area than the area of the proximal surface (34) that includes the groups (26–30) of holes, and avoids problems due to pelvic bone (80) interposition.

25 Claims, 3 Drawing Sheets

DIVERGING GYNECOLOGICAL TEMPLATE

TECHNICAL FIELD OF THE INVENTION

The present invention relates in general to treatment of cancer through the use of interstitial implants through the skin, and more particularly to a diverging gynecological template for radioactive interstitial and intracavitary implants of the cervix.

BACKGROUND OF THE INVENTION

The treatment of locally advanced cancer of the cervix with radiation has been significantly improved with the introduction of perineum templates for the application of both intracavitary and interstitial transperineal and parametrial implants. Conventional templates that have been developed for this purpose are the Syed-Neblett and MUPIT templates. A full description of these prior art templates may be found in Martinez, A., Cox, R. S., and G. K. Edmundson, "A Multiple-Site Perineal Applicator (MUPIT) for Treatment of Prostatic, Anorectal and Gynecologic Malignancies," *Int. J. Radiat Oncol., Biol., Phys.* 10:297-305 (1985); and Syed, A.M.N., Puthawala, W., Neblett, D.L., et al., "Transperineal Interstitial-Intracavitary 'Syed-Neblett' Applicator in the Treatment of Carcinoma in the Uterine Cervix," *Endocuire Hyperther. Oncol.* 2:1-13 (1987).

Problems have been encountered in using the commercially available Syed-Neblett templates. First, it is often impossible to insert the needles through the peripheral rows of this template because of anatomic limitations, in particular pelvic bone interposition. In this case, the lateral parametria and pelvic sidewalls do not receive an adequate radiation dose. Second, there has been seen significant crowding and "coning down" of the needles at the cephalad ends because of interference with the ischial tuberosities and associated ligaments. This leads to significant dose inhomogeneities, especially when a central tandem is also used. Finally, the one-centimeter spacing between needles within the treatment volume results in a large number of needles that must be correctly identified on the films for dosimetry.

The MUPIT device is an attempt to provide an all-purpose template for the interstitial radiotherapy of cervical, rectal, prostate and female urethral cancer. The MUPIT template is relatively large and is provided mostly with needle holes that are parallel to the obturator. It thus has the same coning-down and pelvic bone interposition problems as the Syed-Neblett template. In the MUPIT template, the outer rows of needle holes are angled; however, the holes for the outer needles are four centimeters lateral to the center of the template. Often, the anatomy does not allow the insertion of the needles as far laterally as both designs demand. A need has therefore arisen for a novel gynecological template that will cure the problems inherent in the Syed-Neblett and MUPIT designs.

SUMMARY OF THE INVENTION

One aspect of the invention comprises a diverging template for radioactive therapy of cancer within an internal tumor volume by interstitial implants through the skin. The template includes a proximal surface for positioning adjacent the skin, and a distal surface opposite the proximal surface. A plurality of holes are formed in the template block from the distal surface to the proximal surface for guiding respective needles through the skin and into the tumor volume. These holes comprise at least a first and second group, each hole of the first group spaced from an axis of the template and forming a first angle therewith that diverges from the distal surface to the proximal surface. Each hole of the second group is also spaced from the axis and forms a second angle therewith the axis that is greater than the first angle. Use of needles in the first and second groups allows the uniform radioactive treatment of the tumor volume throughout a cross-sectional area that is larger than that area of the proximal surface containing the first and second groups of holes.

In a preferred embodiment, the template of the invention has four groups of holes, diverging at zero, three, six and nine degrees, respectively. These holes create a needle pattern that diverges in a lateral direction, but not in a vertical direction. In the treatment of cervical cancer, this lateral divergence avoids pelvic bone interposition and the "coning down" effects created by the ischial tuberosities and associated ligaments. Further, since the template only diverges in a lateral direction, the rectum and the bladder are avoided. It has been found that an effective uniform dosage of the cervix and parametrial can be obtained with a needle spacing in the internal volume of 1.5 centimeters. Because of the diverging nature of the template, this translates back to the proximal surface of the template to a spacing of only about 1.0 centimeter between members of adjacent groups of needles. The reduced area of the template has a lateral dimension of only 3.0 centimeters when measured from the axis of the template to its periphery.

BRIEF DESCRIPTION OF THE DRAWINGS

Other aspects of the invention and their advantages will be discerned from the following detailed description when taken in conjunction with the drawings in which.

DETAILED DESCRIPTION OF THE INVENTION

Figure 1:
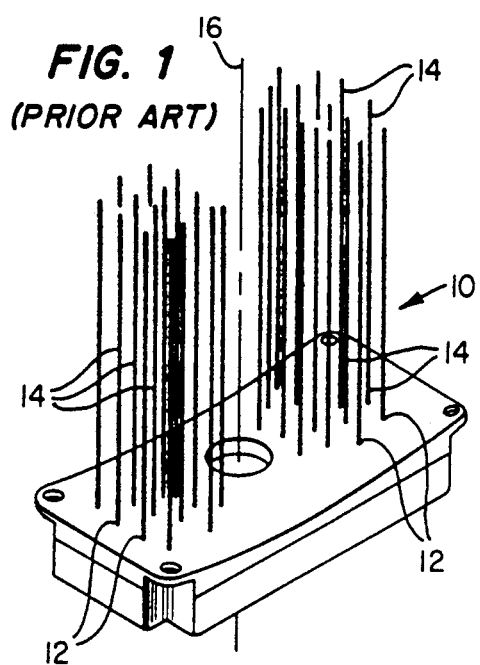
FIG. 1 is an isometric view of the prior art Syed-Neblett template with needles inserted to show their parallel arrangement.

Referring first to FIG. 1, an isometric view of the prior art Syed-Neblett gynecological template is shown generally at 10. The prior art template 10 has a plurality of needle holes 12 that are each perpendicular to a vaginal axis 16. Each of a plurality of needles 14 are inserted through respective holes 12, and therefore are inserted through the perineum in parallel with each other. The spacing of the Syed-Neblett needles within the internal treatment volume is designed to be approximately one centimeter. The Syed-Neblett design, as previously mentioned, has the problems of pelvic bone interposition because of the template's wide lateral extent, as well as "coning down" due to interference with the ischial tuberosities and associated ligaments.

Figure 2:
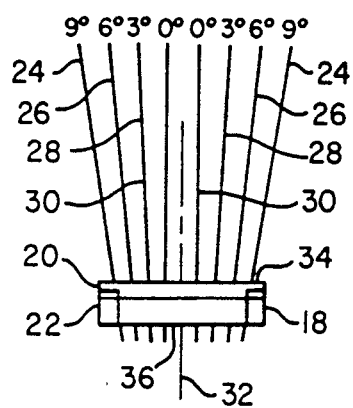
FIG. 2 is a schematic elevational view of a gynecological template according to the invention, as assembled with two needles in each of four groups to show the lateral angular divergence of the needles.

A simplified elevational view of a diverging gynecological template 18 according to the invention is shown in FIG. 2. The template 18 comprises a proximal half 20 and a distal half 22. A plurality of needle holes (not shown; see FIG. 4) are bored through halves 20 and 22 for the insertion of respective needles 24–30, of which only eight are shown for the sake of clarity. In a preferred embodiment, the needles 24–30, and the holes associated with them that will be later described, are grouped in at least four groups. A first group includes needles 30 that make an angle relative to a template axis 32 of zero degrees. The second group is laterally spaced from the axis 32 by an amount greater than needles 30 and make a diverging angle therewith, in a distal-proximal direction, of three degrees. The third group includes needles 26, which are more laterally removed from the axis 32 than the needles 28, and make a diverging angle with the axis 32 of six degrees. The fourth group includes needles 24, which are farthest removed from the axis 32 in a lateral direction and make an angle of nine degrees. A proximal surface 34 of the proximal half 20 is substantially perpendicular to the axis 32. A distal surface 36 of the distal half 22 is opposed to the proximal surface 34.

Since the needles 24–30 diverge in a cephalad or proximal direction from the distal surface 36 to the tips thereof, an area inside the treatment volume that lies in a plane parallel to the proximal surface 34, and containing the needles 24–30, will be larger than an area on the proximal surface 34 containing needles 24–30. This provides advantages in inserting the needles past pelvic bone structure as will be later described.

Figure 3:
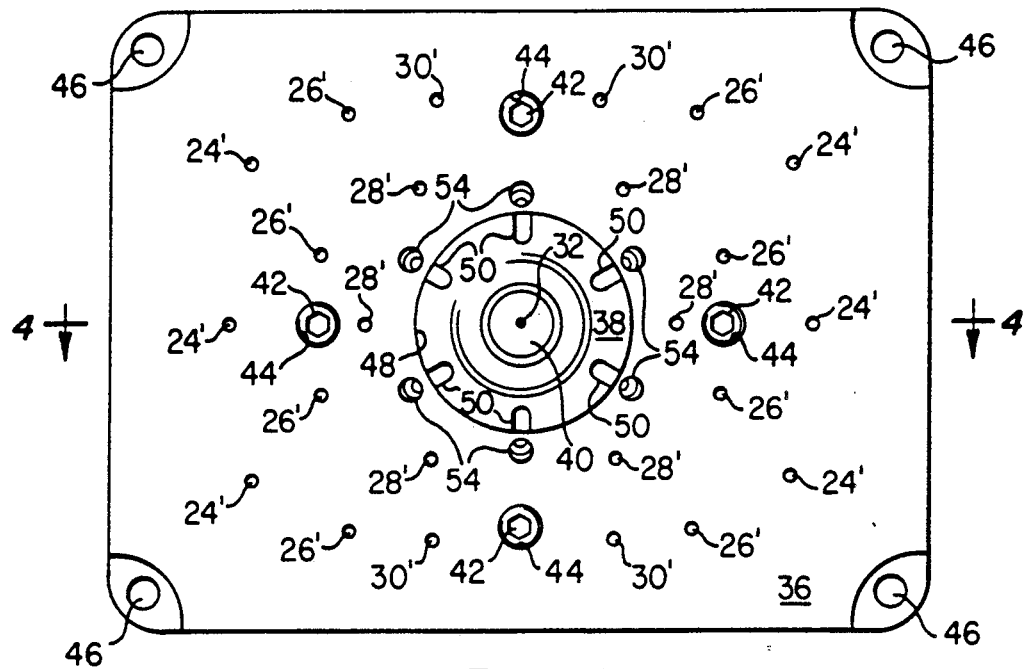
FIG. 3 is a plan view of the distal surface of a preferred embodiment of the template according to the invention, as fitted over a distal end of an obturator.

FIG. 3 is a distal plan view of the template 18, as shown assembled with a vaginal obturator 38 and a central tandem 40. The halves 20 and 22 (not shown; see FIGS. 2 and 4) of the template 18 are machined or otherwise formed from a hard nylon-like material sold under the trademark "DELRIN". "DELRIN" is preferred because it does not expand in sterilizing solutions. The halves 22 and 20 (see FIG. 2) are held together by four allen screws 42 that fit within respective recesses 44. The template 18 is shown in the illustrated embodiment to be rectangular, although other shapes could also be used. Each corner of the template 18 is provided with a suture hole 46 for the attachment of the template 18 to the perineum.

A central bore 48 passes from the distal surface 36 to the proximal surface 34 (see FIG. 2) and is sized to closely receive the vaginal obturator 38. In turn, a bore passes coaxially through the obturator 38 to closely receive a central tandem 40. A plurality of V-shaped grooves 50 in the outside surface of the obturator 38 are each designed to receive respective needles like the needles 24–30 shown in FIG. 2; these needles are used in the instance that no central tandem 40 is employed.

Four sets of holes 24', 26', 28' and 30' are drilled through the template block 18 at various angles to the axis 32. Each hole 24' is drilled at a lateral angle of nine degrees relative to the axis 32, with the angle opening from the distal surface 36 to the proximal surface 34 see FIG. 2). In a like manner, each hole 26' is drilled at an angle of six degrees relative to the axis 32, and each hole 28' is drilled at an angle of three degrees relative to the axis 32. Finally, each hole 30' is drilled at an angle of zero degrees relative to the axis 32.

Each group 24'-30' of holes is drilled through the template 18 so as to be respectively radially equidistant from the axis 32. Further, the hole groups 24'-30' are drilled to be offset from each other to give a more uniform distribution within the tumor volume. Thus, going from left to right, there are three holes 24', four holes 26', three holes 28', two holes 30' above and below the left holes 28', two holes 30' on the right side, three holes 28' somewhat to the right of and sagitally interior of the holes 30', four holes 26', and three rightmost holes 24'. Any hole 24' is spaced from the nearest hole 26' by approximate 10 millimeters, and from the nearest hole 28' by approximately 15 millimeters. The lateral distance from the outmost hole 24' to the axis 32 is approximately 29 to 30 millimeters, a much smaller measurement than the prior art Syed-Neblett or MUPIT templates. In general, the spacing between members of an adjacent set of holes is approximately ten millimeters.

To affix any needles within the grooves 50, as in where intracavitary placement of the needles is desired, six Allen screws 54 are screwed down within respective bores that are drilled radially inwardly from the distal surface 36 until they open on the bore 48 and meet with respective grooves 50 in the obturator 38. These screws 54 also act to clamp the obturator 38 to the template 18, whether or not intracavitary needles are used.

Figure 4:
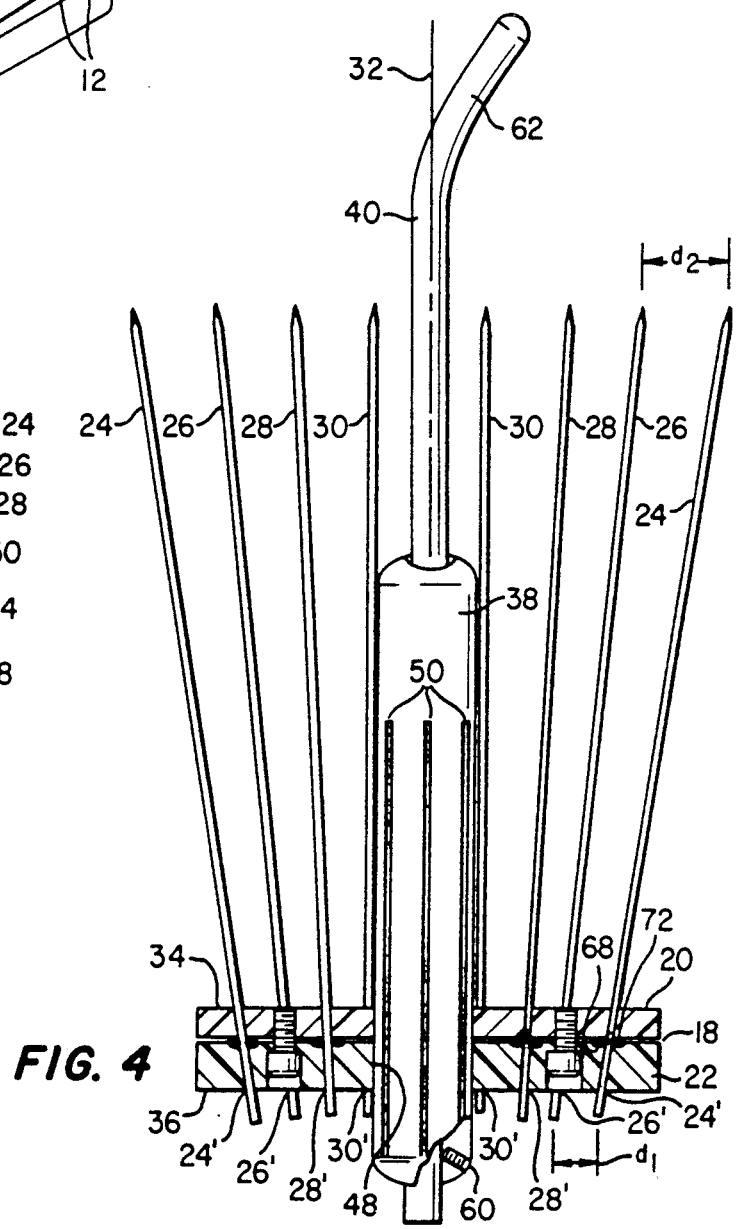
FIG. 4 is a part-elevational, part-sectional view with parts broken away of the template, obturator, tandem and needles, corresponding to line 4—4 of FIG. 3.

Referring now to FIG. 4, a part elevational, part sectional view corresponding to line 4—4 of FIG. 3 is shown with a plurality of needles 24–30 clamped in place within respective holes 24'-30'. Once again, only eight needles 24–30 are shown for clarity. The needles 24–30 are about 20 centimeters long and are hollow for receiving radioactive isotopes.

The obturator 38 is clamped to the central tandem 40 by means of an Allen screw 60 that is received within an appropriate bore. The central tandem 40 is a hollow metal rod approximately six millimeters in diameter. The cephalad portion 62 thereof is angled from the axis 32 in order to better conform to the anatomy of the uterus. While the cephalad end 62 is shown bent in a lateral direction for illustration, in actual use it is turned to bend in an anterior direction.

FIG. 4 also demonstrates the diverging effect of the needles 24–30. As previously noted, the distance $d_1$ between respective members of adjacent courses or groups of holes 24' and 26' as measured on the distal surface 36 of the template 18 is approximately 10 millimeters. Because the needles in different groups are angled outwardly at different angles with respect to the axis 32, the distance $d_2$ at the tips of the needles is approximately 15 millimeters. Thus, for a relatively small template area, a relatively large tumor volume can be uniformly treated.

Figure 5:
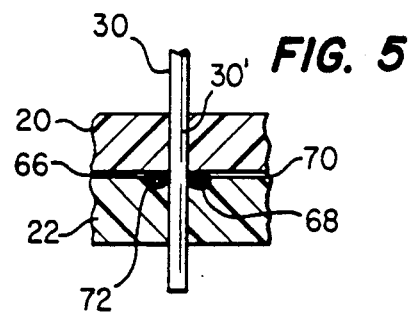
FIG. 5 is a detail of FIG. 4 showing the gripping action of an O-ring around a respective needle.

A preferred method of affixing the needles in place is more particularly illustrated in FIG. 5. Using as an example a needle 30, a seat 68 is formed round the bore 30' in a proximal face 70 of the distal block half 22. A distal face 66 of the proximal half 20 is flat. The seat 68 provides a guide for placing an O-ring 72 which has a much greater thickness in the distal-proximal direction than seat 68. Hence, when the distal half 22 is bolted tightly against the proximal half 20, the O-ring 72 is squeezed inwardly against the walls of the needle 30, thus holding the needle 30 in place. This method of affixing the needles 24-30 places no undue strain upon them, as the angles of the needles 24-30 with respect to normal are always less than ten degrees.

In another embodiment of the invention, the template halves 20 and 22 are replaced with a unitary rubber template (not shown). The rubber template has holes like those of 24'-30' and a bore like bore 48, but with diameters somewhat smaller than the respective ones of halves 20 and 22. The holes and bore are sized such that the needles 24-30 and the obturator 38 will be able to slide through them with aid of a lubrication such as soapy water, but will be firmly held in place once the lubrication dries.

Figure 6:
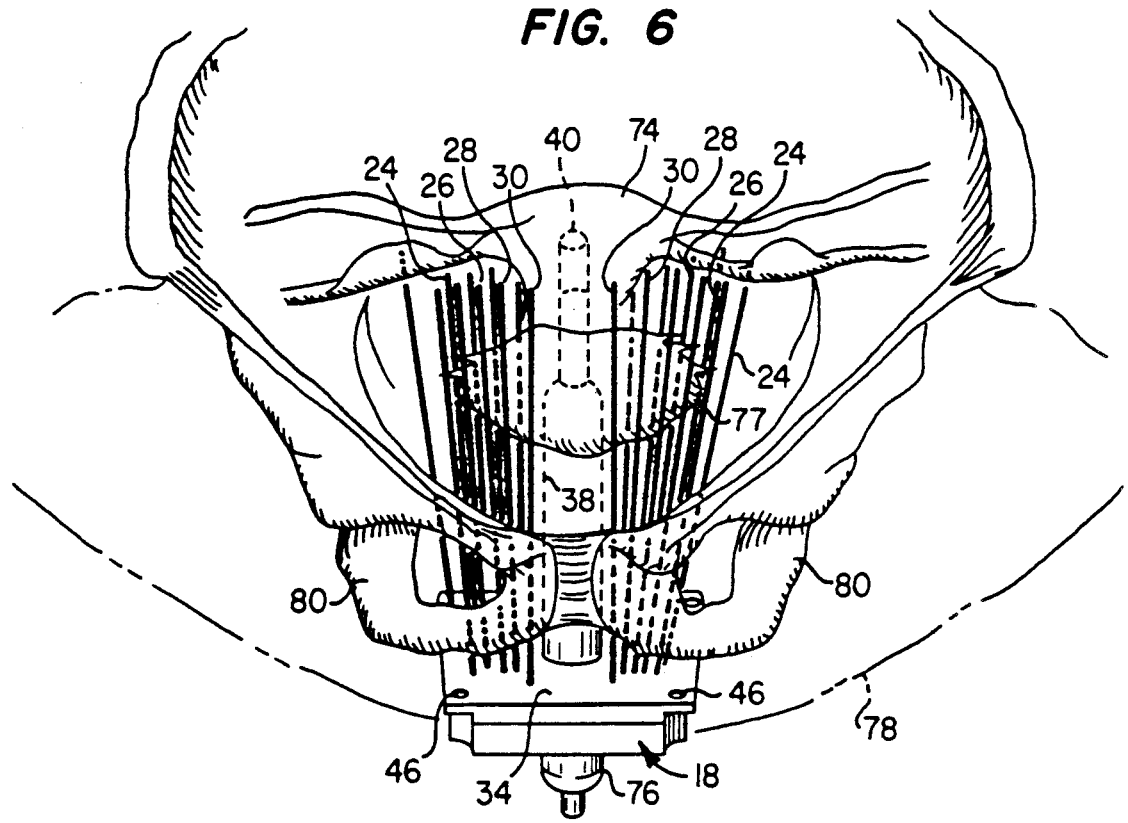
FIG. 6 is schematic anterior view of the female pelvis, uterus and bladder showing the relative positioning of implant needles relative to these anatomical structures according to the invention.

The operation of the invention can best be described with the aid of FIG. 6, which is a schematic interior view of certain anatomical structures of the pelvic region of a female patient. The emplacement procedure of the apparatus is as follows. In most cases, a central tandem 40 will be intracavitally employed to give a radioactive dosage to the interior of the uterus 74. If this is the case, the uterus 74 is first sounded to determine its size and shape so that the correct type and size of tandem 40 may be used. In the surgical arena, the tandem 40 is first inserted through the vagina and cervix into the uterus as shown by the phantom lines. Next, the obturator 38 is vaginally inserted over the tandem 40 such that a distal end 76 thereof protrudes from the vaginal opening by a substantial amount. The obturator 38 is then affixed to the tandem 40 with the aid of the Allen screw 60 (FIG. 4).

The halves 20 and 22 of the template block are bolted together so as to include the O-rings 72 as emplaced on their respective seats 68. The halves are not bolted so tightly together that the needles 24-30 may not pass through the holes 24'-30'(FIG. 4). Once assembled in this manner, the template 18 is fitted over the distal end 76 of the obturator and is positioned against the perineum, which is indicated in FIG. 6 by a dashed line 78. The template 18 is then affixed to the obturator 38 by means of the Allen screws 54 (FIG. 3). To keep the assembly in place, the template 18 is then sutured to the perineum 78 by means of silk sutures and the suture holes 46.

The assembly is now ready for the insertion of needles 24-30 in an array determined by the extent of the tumor. Cervical cancer usually spreads along the broad ligament of the uterus 74 in a lateral direction. The diverging array of the needles 24-30 allows a higher radioactive dose to be given to the lateral parametria and lymph nodes associated with the pelvic sidewalls without increasing the dose to the bladder 77 and the rectum (not shown; posterior to the uterus 74).

Since the needles diverge only in a lateral but not in a sagital direction, the mechanical interference of the ischial tuberosities 80 and their associated ligaments (not shown) is avoided. The present invention therefore allows radioactive therapy of the cervix, the broad ligament, lateral parametria and associated pelvic lymph nodes without problems due to pelvic bone interposition or "coning down" caused by the pelvis and related structure.

Figure 7:
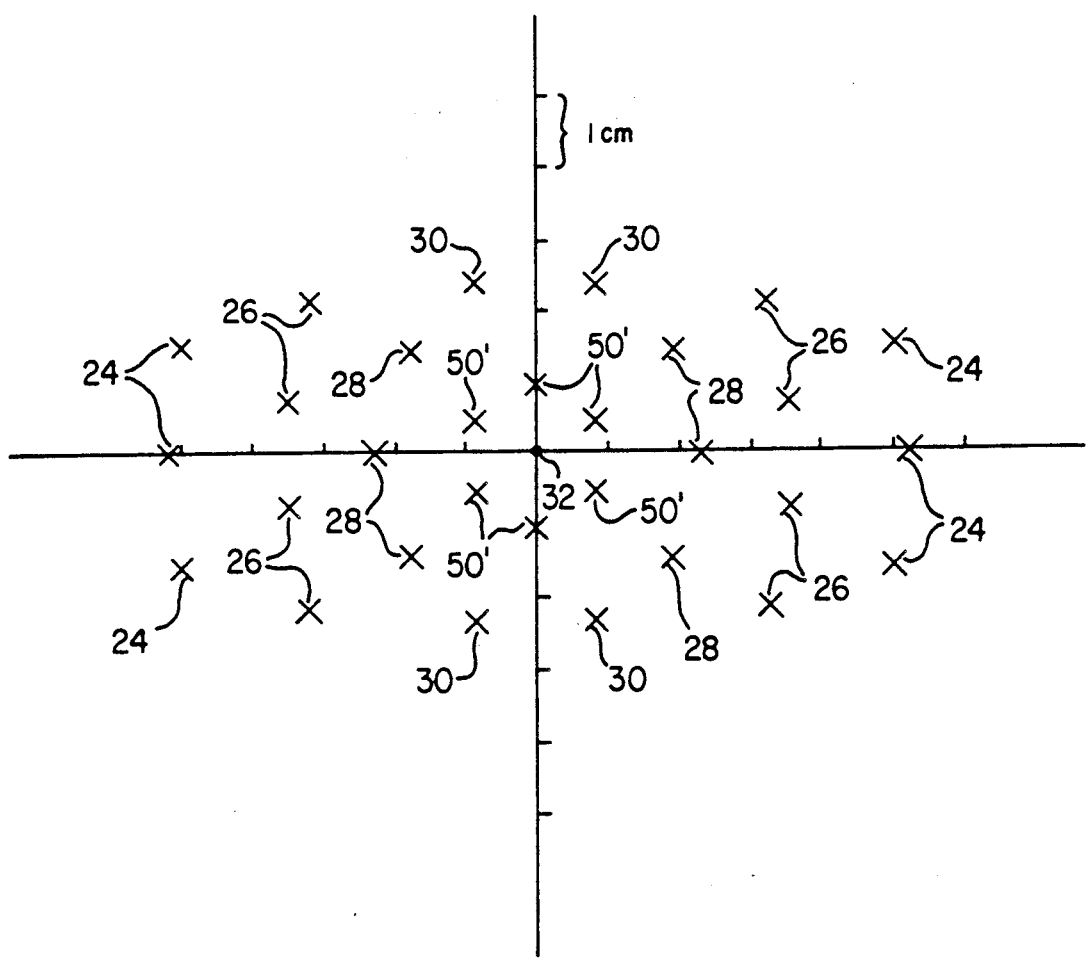
FIG. 7 is a schematic diagram showing the distribution of deployed needle tips in a cervical plane that is perpendicular to the template axis.

A distribution of the needle tips in a cervical plane perpendicular to the axis 32 parallel to the proximate template surface 36 (FIG. 3) is shown in FIG. 7. Each group of needles 24-28 are formed concentric circular segments having respective constant radii to the axis 32. Needles 30 do not diverge, and their tips end up on the circular locus containing needles 28. Needle 50' (See FIG. 7) are optionally used intracavitally to the cervix and correspond to channels 50 (FIG. 3).

In some instances, the cervical cancer will have closed the cervix, and in these cases, the central tandem 40 is not used. In the place of the central tandem, a set of up to six needles 50' inserted through respective channels 50 (FIGS. 3-7) and clamped by screws 54 to be positioned intercavitally to the vagina and cervix.

Once the array of needles 24-30 is in place, the distal half 22 is clamped tightly to the proximal half 20 by means of screws 42 (FIG. 3), and the loading of the radioactive material can commence. In the present invention, the number of needles has been reduced from 38 to 24 (not including the needles along the central tandem) and the interneedle spacing has been increased to 1.5 centimeters. Because of the relatively small difference in angulation of the needles 24-30, and their wider separation, the conversions of the needles is minimal and does not create a "hot spot" centrally as they come close together at the caudal end of the implant. Further, the reduction of the overall number of needles by about 40 percent simplifies the implant technique, and in addition makes identification of the needles on a radio graph much easier. These modifications have lead to clinically achievable dose distributions which are close to the ideal distributions in cases where difficulties were encountered with the prior art designs. To date, the template of the invention has been able to achieve the desired dosimetry without technical difficulty.

In summary, a novel diverging gynecological template has been illustrated and described that provides a uniform radiometric distribution of cervical and related structures, but yet avoids the problems of the prior art designs caused by pelvic bone interposition and template size.

While the illustrated embodiment and its advantages have been described in the above detailed description, the invention is not limited thereto, but only by the scope and spirit of the appended claims.

What is claimed is:

1. Apparatus for the divergent guiding of needles during interstitial implants through the skin, comprising:
    a template having a proximal surface and a distal surface opposite said proximal surface;
    a plurality of elongate needle guiding holes formed in said template from said distal surface to said proximal surface sized to slidably receive respective needles;
    said template having an central vertical axis substantially perpendicular to said proximal surface, said holes comprising at least a first group and a second group, an area on said proximal surface including said first and second groups, each hole of said first group spaced from said axis and forming a first angle therewith that diverges from said distal surface to said proximal surface; and
    each hole of said second group spaced from said axis and diverging from said distal surface to said proximal surface at a second angle with respect to said axis which is greater than said first angle.

2. The apparatus of claim 1, wherein said first angle is about three degrees and said second angle is about six degrees.

3. The apparatus of claim 1 and further comprising a plurality of needles for insertion through selected ones of said holes, said needles, when inserted through said selected ones of said holes, having ends displaced in a proximal direction away from said proximal surface, wherein the spacing between adjacent ones of said ends of needles is less than or equal to approximately 1.5 centimeters.

4. The apparatus of claim 1, wherein the spacing between a hole of the first group and a nearest adjacent hole of the second group is approximately ten millimeters.

5. The apparatus of claim 1, further comprising third and fourth groups of holes, each hole of said third group diverging from said distal surface to said proximal surface at a third angle with respect to said axis which is greater than said second angle;

each hole of said fourth group forming a fourth angle with said axis which is less than said first angle.

6. The apparatus of claim 5, wherein said first, second, third and fourth angles are approximately three, six, nine and zero degrees, respectively.

7. The apparatus of claim 5, wherein the distance on said proximal surface between one of said holes farthest apart from said axis and said axis is more than about 30 centimeters.

8. The apparatus of claim 1, wherein each said group of holes is arranged around said axis at a respective, substantially constant radius therefrom.

9. The apparatus of claim 1, wherein said proximal surface of said template has a lateral dimension and a vertical dimension both perpendicular to said axis, said first and second angles diverging in a lateral direction but not in a vertical direction.

10. The apparatus of claim 1, wherein said second group of holes is spaced further from said axis than said first group of holes.

11. Apparatus for divergently guiding radiotherapeutic needles into a female patient, comprising:

an elongate obturator sized for partial insertion into the vagina and having a distal end;

a template having a proximal surface and distal surface opposite said proximal surface, a central vertical axis substantially perpendicular to said proximal surface;

a central bore of said template passing from said distal surface to said proximal surface and sized to slidably receive said distal end of said obturator;

a plurality of elongate needle guiding holes formed in said template to extend from said distal surface to said proximal surface;

said holes comprising at least a first group and a second group, each hole of said first group spaced from said axis and forming a first angle therewith that diverges from said distal surface to said proximal surface;

each hole of said second group spaced farther from said axis than the holes of said first group, each hole of said second group diverging from said distal surface to said proximal surface at a second angle with respect to said axis which is greater than said first angle.

12. The apparatus of claim 11, wherein said proximal surface of said template has a lateral dimension and a vertical dimension, said first and second groups of holes angularly diverging in a lateral dimension and not in a vertical direction.

13. The apparatus of claim 11, wherein said holes in said template further comprise third and fourth groups, each hole of said third group spaced farther from said axis than the holes of said second group, each hole of said third group diverging from said distal surface to said proximal surface at a third angle with respect to said axis which is greater than said second angle;

each hole of said fourth group forming a fourth angle with said axis which is less than said first angle.

14. The apparatus of claim 13, wherein said first, second, third and fourth angles are approximately three, six, nine and zero degrees, respectively.

15. The apparatus of claim 13, wherein said first, second, third and fourth angles are selected to avoid the interference of the ischial tuberosities and associated ligaments with the penetration of respective needles through said holes into a tumor volume.

16. The apparatus of claim 13, wherein said area of said proximal surface has a lateral dimension of approximately 3 centimeters measured laterally from said axis to the periphery of said area.

17. The apparatus of claim 13, wherein the spacing between one hole of said first group and the closest hole of said third group is approximately fifteen millimeters.

18. The apparatus of claim 11, wherein the spacing between the hole of said first group and the closest hole of said second group is approximately ten millimeters.

19. The apparatus of claim 11, and further comprising a plurality of needles for insertion through selected ones of said holes, each of said needles having an end which, when inserted through a selected one of said holes, is displaced from said proximal surface in a proximal direction, the largest distance between any one of said ends and a next adjacent end being approximately 1.5 centimeters.

20. The apparatus of claim 11, wherein each said group of holes is radially arranged around said axis at a respective substantially constant radius.

21. The apparatus of claim 11, wherein said template comprises a proximate half including said proximal surface and a distal half including said distal surface, a plurality of seats around said holes, said seats defined by at least a preselected half of said template, a plurality of O-rings disposed in respective ones of said seats, each said O-ring operable to grip a respective needle when said halves are substantially compressed together.

22. The apparatus of claim 11, further comprising an elongate tandem, an axial bore in said obturator for fitting said obturator over said tandem, means for affixing said said tandem within said axial bore of said obturator.

23. A method for the divergent guiding of needles into an internal tumor volume, comprising the steps of:

positioning a proximal surface of a template adjacent an area of the skin near said internal tumor volume, a plurality of holes in said template extending from a distal surface of said template to said proximal surface, an axis of said template being substantially perpendicular to said proximal surface;

affixing said template in place;

inserting needles through respective ones of said holes in said template and through the skin into said internal tumor volume, said holes comprising at least a first group and a second group, each hole of said first group spaced from the axis of the template and forming a first angle therewith that diverges from said distal surface to said proximal surface, each hole of said second group spaced from the axis and forming a second angle therewith that diverges from the distal surface to the proximal surface at a second angle greater than the first angle; and responsive to said step of inserting, positioning said needles in an array diverging from the axis of the proximal surface.

24. The method of claim 23, wherein said method employs an elongate obturator, said template having an axial bore for receiving the obturator, and the tumor volume is located in a uterine cancer, the method further comprising the steps of:

partially inserting the elongate obturator into the vagina such that a distal end of the obturator protrudes from the vagina by a substantial amount;

fitting the template over the distal end of the obturator by receiving the distal end thereof into the axial bore of the template;

affixing the template in place adjacent the perineum; and inserting needles through the template through respective holes therein, such that the needles will laterally diverge into the tumor volume; and responsive to said step of inserting needles, avoiding interference from the ischial tuberosities and associated ligaments during the needles' penetration into the tumor volume.

25. The method of claim 23, wherein said proximal surface has a lateral direction and a sagital direction perpendicular to the lateral direction, both the lateral and sagital directions being perpendicular to the axis of the template, the method further comprising the steps of:

inserting the needles through respective holes such that the divergence of the needles from the axis is substantially in said lateral direction.

* * * * *